United States Patent [19]
Suhr et al.

[11] 3,940,690
[45] Feb. 24, 1976

[54] MULTI-PROBE FLUX LEAKAGE TESTING APPARATUS USING SKEWED PROBES

[75] Inventors: Peter J. Suhr, Garden City; Edward D. Spierer, Belle Harbor, both of N.Y.

[73] Assignee: Magnetic Analysis Corporation, Mount Vernon, N.Y.

[22] Filed: Aug. 13, 1974

[21] Appl. No.: 496,926

[52] U.S. Cl. ............................................. 324/37
[51] Int. Cl.² ........................................ G01R 33/12
[58] Field of Search ............................... 324/37, 40

[56] References Cited
UNITED STATES PATENTS

| | | | |
|---|---|---|---|
| 2,036,857 | 4/1936 | Drake | 324/37 |
| 3,504,276 | 3/1970 | Proctor et al. | 324/37 |
| 3,854,085 | 12/1974 | Mansson et al. | 324/37 |

*Primary Examiner*—Robert J. Corcoran
*Attorney, Agent, or Firm*—Pennie & Edmonds

[57] ABSTRACT

In apparatus in which an object moves longitudinally and rotationally with respect to a multi-probe assembly, each probe including a channel-shaped core of magnetic material having spaced sides which are long compared to the thickness thereof and a coil encircling the core, and bipolar signals are developed whose positive and negative excursions correspond to the largest flaw signal of each polarity simultaneously occurring in the probes, the probes of the assembly are arranged in succession along the longitudinal path of travel of the object and skewed with respect to the longitudinal path of travel with an end of one probe adjacent the end of the next probe to yield flaw indications for longitudinal defects which are largely dependent on the depth of the flaw and independent of its length. Accordingly such indications are approximately the same as for short defects of the same depth, thereby yielding indications more nearly corresponding to the severity of the defects. Two or more probe assemblies with the same skew direction may be employed to increase the speed of inspection. If helical flaws of opposite pitch can be present, two probe assemblies of opposite skew directions can be employed.

10 Claims, 10 Drawing Figures

MULTI-PROBE FLUX LEAKAGE TESTING APPARATUS USING SKEWED PROBES

BACKGROUND OF THE INVENTION

In application Ser. No. 367,883 filed June 7, 1973 by Mansson et al., now U.S. Pat. No. 3,854,085 nondestructive testing apparatus of the magnetic flux leakage type is disclosed in which a plurality of electromagnetic pickups or probes simultaneously scan different portions of an object passing thereby. Each probe produces a flaw signal having positive and negative excursions, and is preferably a core of magnetic material having spaced legs with a coil wound around the core. The probe outputs are amplified and the positive and negative portions separately rectified and combined to yield positive and negative signals corresponding to the largest signal of each polarity simultaneously occurring in the probes. These largest signals are added to yield bipolar signals having corresponding positive and negative excursions. The bipolar signals are then supplied to one or more processing channels for producing flaw indications.

In one embodiment a probe assembly having a plurality of longitudinally-spaced probes is mounted on a rotating head through which an object to be tested is passed, e.g. a tube or rod. A magnet on the head produces a transverse magnetic field across the object. Flaws in the object produce leakage flux which is sensed by one or more probes to produce a flaw indication. Two probe assemblies may be diametrically spaced on the rotating head to permit greater speed of travel of the object through the head.

In the specific embodiments of the aforesaid application the probes in a given assembly are in alignment. This has been found to give excellent results in detecting flaws in longitudinal weld seams in tubes, for example, with a high signal-to-noise ratio. Also, spiral defects can be detected for either direction of spiralling, although the signal amplitude may be smaller since a smaller portion of a probe will be effective at a given instant. Other types of flaws can also be detected.

Although capable of giving excellent results under appropriate operating conditions, it has been found that a long shallow longitudinal flaw may give an output signal having an amplitude equal or greater than that for a short deep flaw. In many cases short deep flaws may be more serious than long shallow flaws.

A primary object of the present invention is to provide flux-leakage test apparatus of the foregoing type in which the flaw signal amplitude is largely dependent on the depth of the flaw and independent of its length. Thus the signal amplitude corresponds more closely to the severity of the defect.

SUMMARY OF THE INVENTION

In accordance with the invention, one or more probe assemblies are employed in which the probes each include a channel-shaped core of magnetic material having spaced sides which are long compared to the thickness thereof and a coil encircling the core, and are arranged in succession along the longitudinal path of travel of an object to be tested and skewed with respect to the longitudinal path of travel, with an end of one probe adjacent an end of the next probe respectively. Preferably a side of one probe core is in approximate alignment with a side of the next probe core, in abutting relationship, and the other sides of the respective cores are on opposite sides of the aligned sides. Advantageously the sides of the cores are longer than the lateral spacing thereof, and the thickness of the bottoms of the legs is substantially less than the lateral spacing.

Desirably the relative longitudinal and rotational speeds of the object relative to the probe assembly, and the skew angles of the probes, are predetermined so that a point on the object passing the region of adjacent sides of two probes will pass the other sides of the probes inward from the ends thereof.

Two or more probe assemblies may be circumferentially spaced around the object to be detected, with the probes skewed in the same direction, so as to allow greater speed of travel of the object through the test head while preserving inspection of all points of the object. It is possible, although not common, for objects to have helical flaws of such pitch and direction as to escape detection by probe assemblies skewed in one direction. In such case, two probe assemblies skewed in opposite directions may be employed, with appropriate reduction in the speed of travel of the object through the head.

The skewing of the probes provides small localized detection regions for longitudinal flaws so that the resultant flaw signals have amplitudes which vary primarily with the flaw depth and are relatively independent of flaw length. Thus the signal amplitudes for longitudinal flaws of given depth are approximately the same as for short flaws of the same depth.

The flaw signals are combined in the same manner as described in the above-identified application, but the resultant flaw indications more nearly correspond to the severity of the defects.

DESCRIPTION OF THE SPECIFIC EMBODIMENTS

Figure 2:
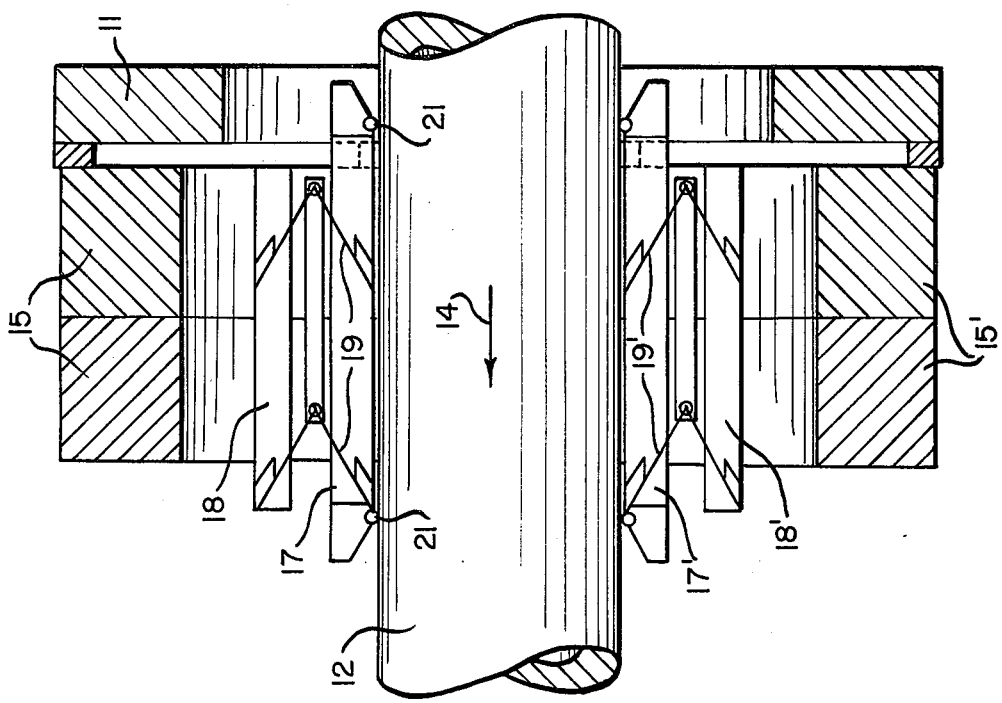
FIG. 2 is a cross-section taken along the line 2—2 of FIG. 1.
Figure 1:
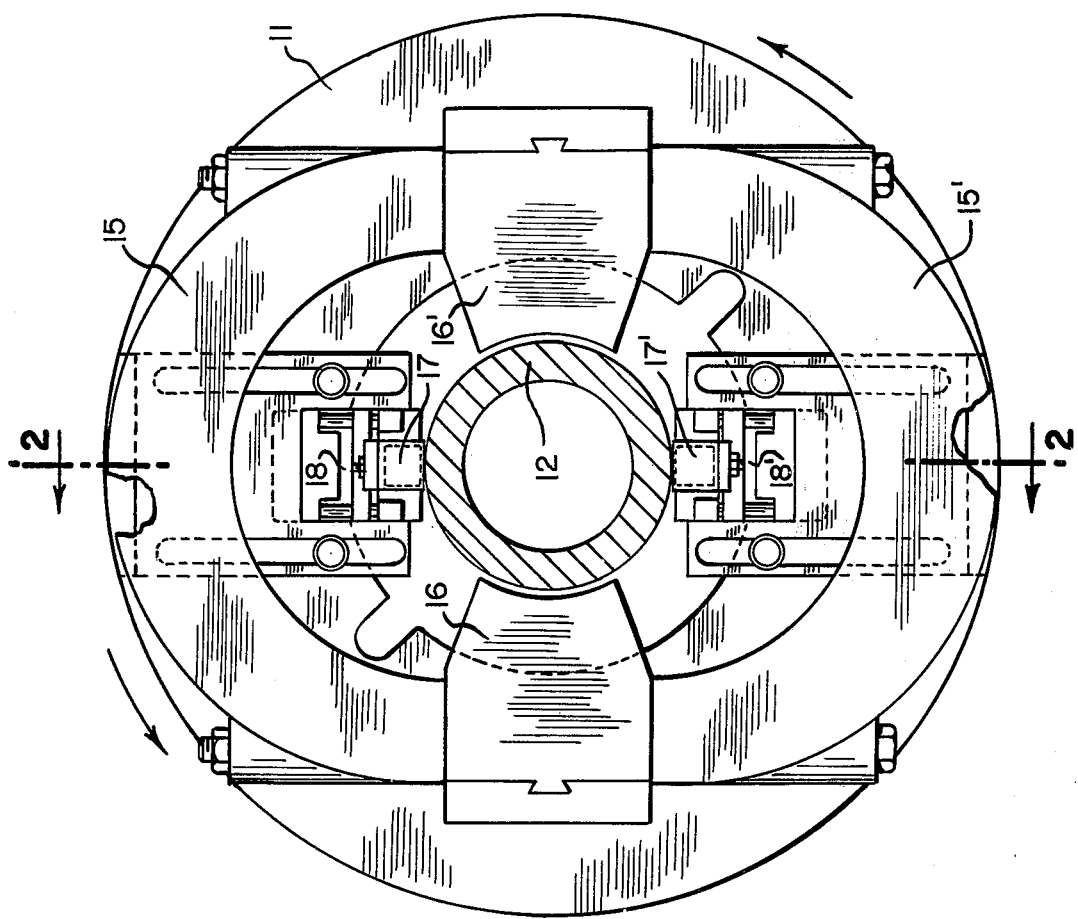
FIG. 1 is a face view of a rotating flux-leakage testing head taken from the left of FIG. 2.

FIGS. 1 and 2 illustrate a rotating head arrangement using probe assemblies in accordance with the invention. A rotating head plate 11 is mounted for rotation on a stationary structure (not shown), such as the structure described in the above-identified application. An object to be tested, here shown as a tube 12, is fed longitudinally through a central opening in the head plate, as indicated by arrow 14. A permanent magnet structure produces a steady state magnetic field across the tube in the region under test. As here shown, pairs of half cylinders 15, 15' are mounted on the head plate 11 with pole pieces 16, 16' clamped therebetween. The pole pieces may be replaceable to permit testing objects of different diameter.

Two probe assemblies 17, 17' are mounted on support members 18, 18' by pairs of springs 19, 19'. The support members are adjustably mounted to permit testing different diameter objects. The mounting means need not be described in detail since it forms no part of the present invention. The probe assemblies 17, 17' have ramp ends to move the assemblies outward if struck by an entering object, and riding shoes 21 which maintain a small air gap between the probes and the object.

Figure 3A:
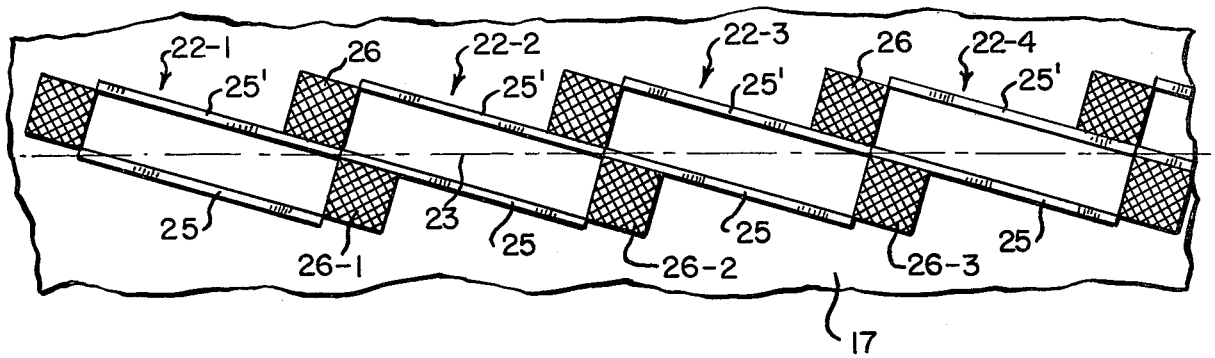
FIGS. 3a and 3b show a portion of the probe assemblies used in FIGS. 1 and 2, with skew angles in opposite directions.
Figure 3B:
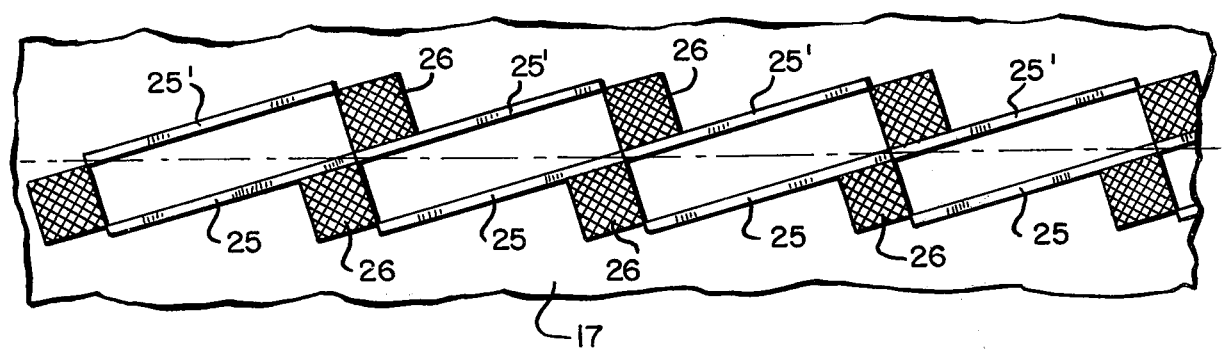

FIG. 3a shows a plurality of leakage flux probes 22 symmetrically arranged in succession along a line 23 parallel to the longitudinal path of travel 14 (FIG. 2) of an object to be tested, and skewed with respect to line 23. The probes may be potted in suitable material to form the probe assembly 17 of FIG. 2. FIG. 3b shows the probes skewed in the opposite direction. The choice of direction will be discussed later.

Figure 4:
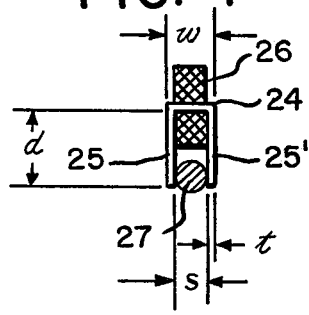
FIGS. 4 and 5 are end and side views of a preferred form of a probe.
Figure 5:
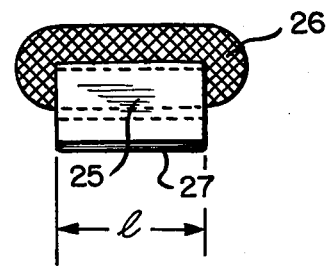

FIGS. 4 and 5 show a presently preferred form of probe. A channel-shaped core 24 of magnetic material such as mumetal is formed with a U-shape cross-section to provide a pair of spaced rectangular sides 25, 25' which are long (dimension l) compared to the thickness $t$ thereof. Preferably the sides are substantially longer than the spacing $s$ therebetween and the thickness at the bottoms of the sides is substantially less than the spacing. A coil 26 is wound around the center top portion of the core. For protection, and to provide a smooth ride, a non-magnetic rod 27 such as carbide may be secured between the sides of the core and extends slightly therebelow.

As an example, and not by way of limitation, in one embodiment the core was formed of mumetal 0.021 inch thick, with a length $l$ of about 0.5 inch and width $w$ about 0.167 inch. The depth $d$ of the sides was about 0.25 inch. Twelve such probes, with a skew angle of about 18°, were employed, yielding an effective test length of about 63. inch. Skew angles of 16° have also been employed.

Figure 6:
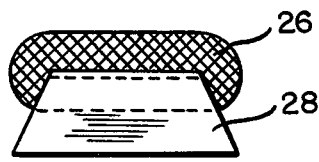
FIG. 6 is a side view of another embodiment of a probe.

FIG. 6 shows a probe in which sides 28 have a trapezoidal shape, as described in the above-identified application. With the probes aligned, this allows close spacing of the cores while allowing room for the coils. Although usable in the skewed arrangement of the present invention, the skewing allows close spacing of probe cores using the rectangular sides of FIG. 5, since the coils are offset as shown in FIGS. 3a, b. The rectangular sides yield more uniform response to defects or flaws passing close to the ends of the core.

As explained in the above-identified application, a flaw passing the two sides of a probe in succession will produce successive positive and negative signal excursions in the associated coil, or vice versa, depending on the direction of coil winding and its circuit connections. In FIGS. 3a and 3b a side of one core is in alignment with a side of the next core, and the other sides of the respective cores are on opposite sides of the aligned sides. Thus in FIG. 3a sides 25' and 25 of probes 22-1 and 22-2 are in alignment, and sides 25 and 25' of the respective probes are on opposite sides. With the aligned sides abutting as shown, no flaws can pass by the assembly without passing over at least one core side.

Figure 7:
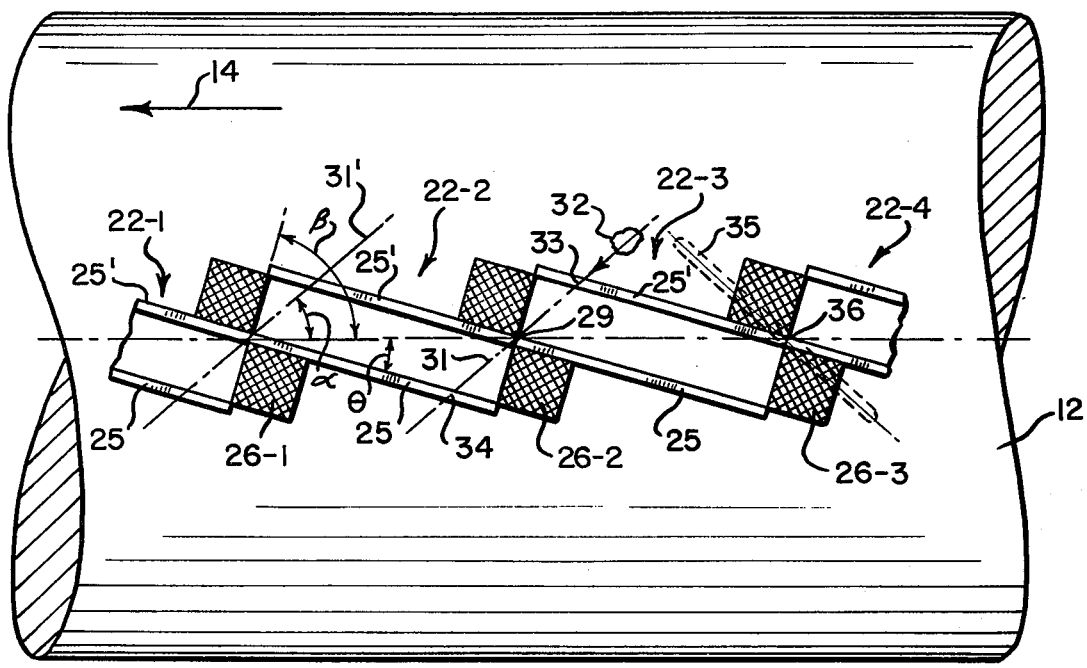
FIG. 7 is a schematic illustrating one path of travel of a defect relative to a probe assembly.

However, as shown in FIG. 7, it is possible for a small flaw to pass over the junction 29 between the abutting sides of adjacent probes. Here line 31 represents the path of travel of flaw 32 relative to the probes. The path will actually be helical with constant longitudinal and rotational speeds. In FIG. 7 the size of the probes relative to object 12 has been exaggerated for clarity, and the path of travel of the flaw at the probes is approximately straight.

When flaw 32 passes point 29, with similar coil winding directions and connections, signals of equal amplitude and opposite polarity will be generated in the coils of probes 22-2 and 22-3, and will cancel out in the associated circuitry described hereinafter in connection with FIG. 9. However, as flaw 32 passes points 33 and 34 in succession, signals of opposite polarity will be produced in the respective probe coils and produce a flaw signal. To insure substantially full amplitude signals, it is preferred to select the relative longitudinal and rotational speeds of the object, and the probe skew angles, so that a point on the object (e.g. flaw 32) which passes the region of adjacent sides of two probes (e.g. point 29) will pass the other sides of the probes inward from the ends of the probes (e.g. points 33 and 34). In mathematical terms, the helix angle $\alpha$ of the path of a point on the object with respect to the probe assembly is less than the angle $\beta$, which is the complement of the skew angle $\theta$.

The aligned abutting arrangement shown is preferred. However, some spacing or overlapping of the adjacent ends of core sides 25 and 25' may be usable. With a small space between the ends, flaws passing over the region of a space may produce signals at the other sides of the cores, as explained in connection with points 33 and 34, with proper choice of longitudinal and rotational speeds. With some overlapping, the no signal area such as at point 29 will be increased, and the overall length of the assembly decreased under otherwise similar conditions.

Ordinarily the direction of probe skewing shown in FIGS. 3a and 3b will be the same in both probe assemblies 17, 17' of FIG. 2, with respect to the object, so as to allow a higher speed of travel of the object through the test head than with one assembly while preserving inspection of all points of the object. The direction of skewing will depend on the directions of longitudinal and rotational movements of the object relative to the probes, as will be understood from FIG. 7.

Occasionally objects may have helical flaws. If the helix angle is small, the flaw may be detected similarly to a longitudinal flaw as will be explained in connection with FIG. 8. It is possible, although perhaps rare, for such flaws to have helix angles equal or near the angle at which a point on the object passes the probe assembly. If the direction of travel of the flaw is similar to path 31, the leading and trailing ends of the flaw, or variations in the flaw, will produce flaw signals. However, if the flaw spirals in the opposite direction as it passes the probe assembly it is possible for it to pass through the test head without detection. For example, assume a helical flaw such as shown at 35, or a short flaw of the same angle, passing the junction point 36 between probes 22-3 and 22-4 at or near the flaw angle. If the flaw angle is exactly equal to the angle of travel of a point on the object past the probe assembly, the flaw will intersect the probe assembly only at point 36 and no flaw signal will be generated. If not exactly equal, the flaw may intersect only one side of probe 22-3 or 22-4, thereby generating only a unipolar signal. In such case the probes of the two assemblies 17 and 17' in FIG. 2 may be skewed in opposite directions as illustrated in FIGS. 3a and 3b, so that helical flaws traveling in either direction past the test head may be detected. The speed of travel of the object through the test head may be reduced to insure that all points on the object are inspected before leaving the test region.

Figure 8:
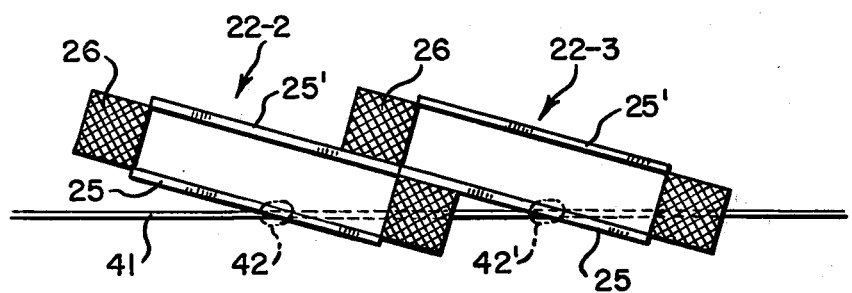
FIG. 8 illustrates effective zones of detecting longitudinal defects.

Referring to FIG. 8, a long longitudinal flaw 41 is assumed. If probes 22-2 and 22-3 were in alignment, the entire length of sides 25 and 25' would be effective to produce flaw signals. However, with the skewed probes only leakage flux in the restricted intersecting regions 42, 42' is effective to produce flaw signals of one polarity. As the probes rotate, similar regions of sides 25' will be effective to produce flaw signals of the opposite polarity. The amplitude of these signals will vary with the depth of the flaw, but will be largely independent of the flaw length. Thus the flaw signal amplitude will be similar to that for defect 32 in FIG. 7, if the flaw depth is the same. Stated differently, the output obtained for a small hole and a serious defect of considerable length is equalized, whereas the output for a small hole is much greater than that for a shallow defect of considerable length.

If the longitudinal flaw 41 varies in severity along its length, the signals at areas 42, 42' will be different in amplitude although occurring simultaneously. As later described in connection with FIG. 9, only the largest signal will be effective in producing a flaw indication. The same will be true when sides 25' of the probe cores become effective. To this end, the coils of the probes are wound in the same direction and connected to similar input terminals of the respective amplifiers.

Figure 9:
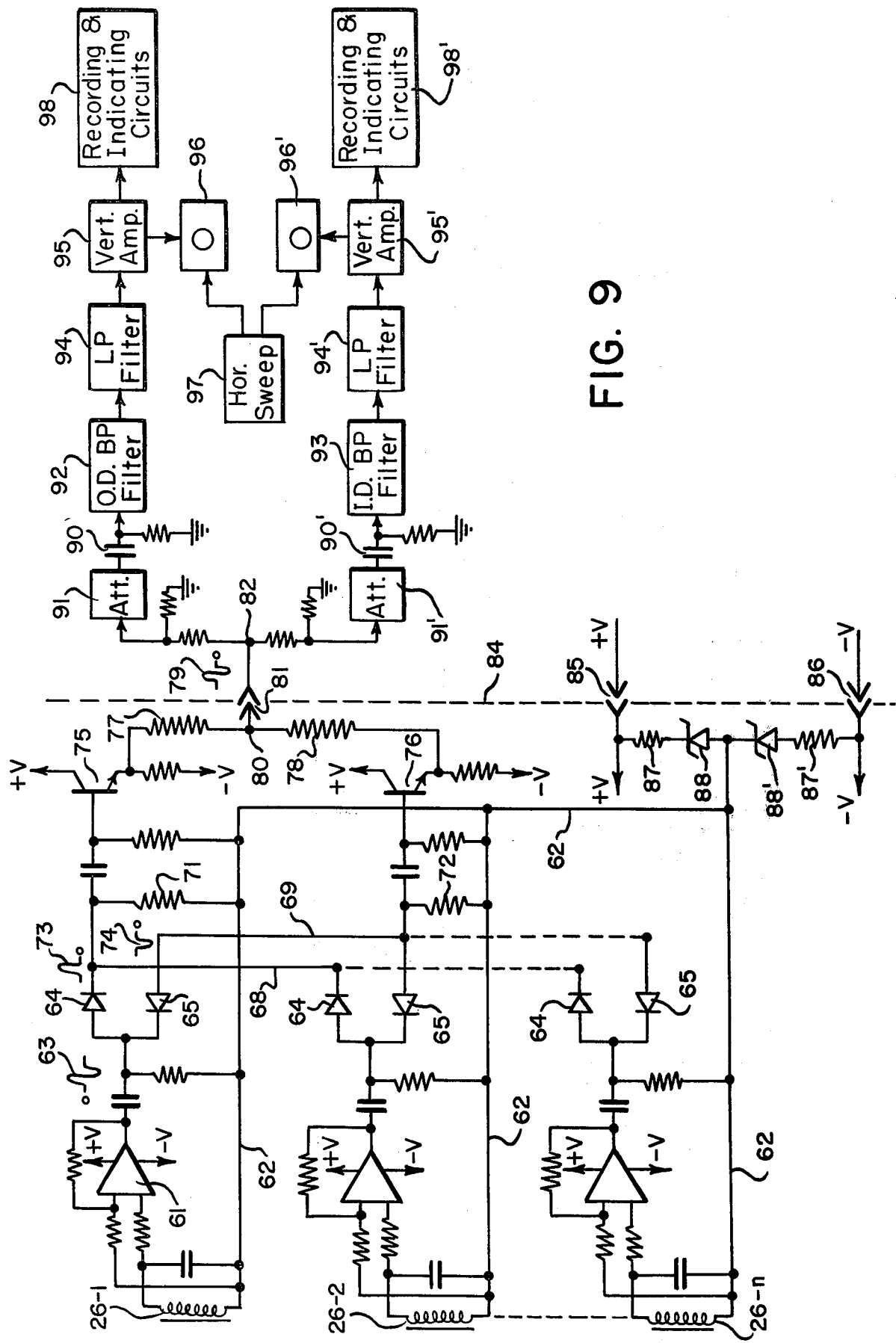
FIG. 9 is a circuit diagram of processing circuits used with the apparatus of FIGS. 1 and 2.

Referring to FIG. 9, this circuit is the same as in FIG. 8 of the above-identified application, and the same numerals are used here, except for the designation of the probe coils. The description will be abbreviated, since reference may be made to that application for greater detail.

Probe coils 25-1, 26-2 . . . 26-n represent the number of probes used in a given application. The output of probe 26-1 is amplified in 61 and the flaw signal output indicated at 63 is supplied to a pair of oppositely poled rectifiers, here shown as diodes 64, 65. The circuits for the other probes are the same.

Positively-poled diodes 64 from all the probe channels are connected together by line 68, and negatively-poled diodes 65 by line 69. Each set of diodes is returned to reference line 62 through respective resistors 71, 72. Thus the diodes 64, 65 act as negative and positive signal clippers, yielding positive signal portions in line 68 as indicated at 73, and negative signal portions in line 69 as indicated at 74.

The circuit functions to produce in lines 68, 69 only the largest positive and negative signals simultaneously applied to respective sets of diodes, and all diodes except those passing these largest signals are back-biased so that they become essentially open circuits and do not contribute noise in the connecting lines or present any load on the conducting diodes. As the probes produce flaw signals occurring at different instants in time, only the largest positive signal occurring at any one instant will be passed, and only the largest negative signal occurring at any one instant will be passed, with time differences the same as their original time differences.

The signals in lines 68, 69 are supplied to transistors 75, 76 forming an adder circuit. The transistors are connected as emitter followers with respective output resistors 77, 78 connected together. The adder circuit combines the largest positive and negative signals occurring at corresponding instants in lines 68, 69 to form a bipolar signal 79 at the junction point 80. As positive and negative signals occur in lines 68, 69 at different instants in time, they are added to a zero voltage base to form corresponding bipolar signals. These bipolar signals are usually found to be approximately single sinusoidal cycles, or at least contain fairly strong sinusoidal components, thereby enabling useful filtering as will be described later.

Depending on the position of a flaw with respect to the probe sides, or a plurality of flaws producing simultaneous signals, the positive and negative excursions of the resultant bipolar signal at point 80 may be approximately equal as shown at 79, or the amplitudes of the positive and negative excursions may be unequal. In some cases the peaks may be more widely separated. Subsequent circuits will commonly include capacitor couplings which will eliminate the DC components, for example as shown at 90, 90', so that the waveforms will contain substantial sinusoidal components.

As described in the above-identified application, all components to the left of line 84 may be carried on the rotating head of the test equipment, and the added signals at point 80 supplied through a slip ring indicated by the symbol 81 to a connection 82 on stationary mounting means for the head.

Plus and minus voltages for the amplifiers may be supplied through slip rings indicated by symbols 85, 86 to the rotating head, and a virtual ground for line 62 developed by resistors 87, 87' and Zener diodes 88, 88'. If desired, an additional slip ring could be employed to connect line 62 to ground.

Flaw signals at point 82 may be supplied to one or more processing channels for indication, including recording and sorting as desired. Here, all signals are supplied to two independent processing channels to enable separation of O.D. and I.D. flaws.

Each channel includes an attenuator 91, 91' for adjusting the sensitivity. The upper channel includes a bandpass filter 92 covering the band of frequencies expected to be produced by O.D. flaws. The lower channel includes a bandpass filter 93 covering the band of frequencies expected to be produced by I.D. flaws. Each bandpass filter may be designed to provide several selectable bandpass regions to meet the requirements of different applications. Low pass filters 94, 94' may be provided to eliminate high frequency transients unrelated to or not necessary for flaw detection. The resultant flaw signals are amplified in 95, 95' and supplied to the vertical deflection circuits of oscilloscopes 96, 96'. Suitable horizontal sweeps are supplied to the oscilloscopes from 97. Thus O.D. and I.D. flaws may be separately observed.

The outputs of amplifiers 95, 95' may be supplied to recording and indicating circuits 98, 98' in accordance with conventional practice, and these circuits may include threshold circuits actuating an alarm, marker or segregator whenever either the positive or negative portions exceed a predetermined value.

As will be understood from the foregoing, with the skewed probe arrangement of the present invention the flaw signals developed by the circuit of FIG. 9 will more nearly correspond to the severity of flaws, whether long or short, which is advantageous in many practical applications.

The invention has been described in connection with specific embodiments thereof. It will be understood that changes may be made in the specific configurations, as deemed desirable to meet the requirements of a particular application.

We claim:

1. Multi-probe flux leakage testing apparatus for detecting flaws in an object relatively moving longitudinally and rotationally with respect to the probes which comprises
   a. means for producing a steady state magnetic field in said object in the test region thereof,
   b. a plurality of leakage-flux probes for producing respective signal outputs having positive and negative excursions corresponding to flaws passing thereby in said test region,
   c. said probes each including a channel-shaped core of magnetic material of generally U-shaped cross-section and having spaced sides which are long compared to the thickness thereof and a coil encircling the core for producing said signal outputs,
   d. said probes being arranged in succession along the longitudinal path of travel of a said object and skewed with respect to said longitudinal path of travel with an end of one probe adjacent an end of the next probe respectively,
   e. means for rectifying and combining the positive portions of the signals from said probes and rectifying and combining the negative portions of the signals from said probes to yield positive and negative signals corresponding to the largest signal of each polarity simultaneously occurring in said probes,
   f. adding means for adding said largest positive and negative signals to yield bipolar signals having corresponding positive and negative excursions,
   g. and circuit means responsive to said bipolar signals for indicating flaws in a said object.

2. Apparatus according to claim 1 in which said channel-shaped cores are substantially longer than the spacing between the sides thereof and the thickness of the bottoms of the sides is substantially less than said spacing.

3. Apparatus according to claim 1 in which at adjacent ends of said cores a side of one core is adjacent a side of the next core, and the other sides of the respective cores are on opposite sides of the core sides which are adjacent.

4. Apparatus according to claim 3 in which the longitudinal and rotational speeds of an object to be tested relative to the probes, and the skew angles of the probes, are predetermined so that a point on the object passing the region of adjacent sides of two probes will pass the other sides of the probes inward from the ends thereof.

5. Apparatus according to claim 1 in which a side of one core is in approximate alignment along the skew angle with a side of the next core, and the other sides of the respective cores are on opposite sides of the approximately aligned sides.

6. Apparatus according to claim 5 in which said aligned sides substantially abut.

7. Apparatus according to claim 1 including two circumferentially-spaced sets of said probes, the skewing of the probes of one of said sets being in the opposite direction to the skewing of the probes of the other of said sets with respect to said object.

8. Multi-probe flux leakage testing apparatus for detecting flaws in an object relatively moving longitudinally and rotationally with respect to the probes which comprises
   a. means for producing a steady state magnetic field in said object in the test region thereof,
   b. a plurality of leakage-flux probes for producing respective signal outputs having positive and negative excursions corresponding to flaws passing thereby in said test region,
   c. said probes each including a channel-shaped core of magnetic material of generally U-shaped cross-section and having spaced sides which are long compared to the thickness thereof and a coil encircling the core for producing said signal outputs,
   d. said probes being symmetrically arranged in succession along a line parallel to the longitudinal path of travel of a said object and skewed with respect to said line with a side of one core in alignment along the skew angle with a side of the next core and with adjacent ends abutting, the other sides of the respective cores being on opposite sides of the aligned sides,
   e. means for rectifying and combining the positive portions of the signals from said probes and rectifying and combining the negative portions of the signals from said probes to yield positive and negative signals corresponding to the largest signal of each polarity simultaneously occurring in said probes,
   f. adding means for adding said largest positive and negative signals to yield bipolar signals having corresponding positive and negative excursions,
   g. and circuit means responsive to said bipolar signals for indicating flaws in a said object.

9. Apparatus according to claim 8 in which the longitudinal and rotational speeds of a said object relative to the probes, and the skew angles of the probes, are predetermined so that a point on the object passing the abutting region of sides of two cores will pass the other sides of the cores inward from the ends thereof.

10. Apparatus according to claim 8 including two circumferentially-spaced sets of said probes, the skewing of the probes of one of said sets being in the opposite direction to the skewing of the probes of the other of said sets with respect to said object.

* * * * *